United States Patent [19]
Cathignol et al.

[11] Patent Number: 4,962,753
[45] Date of Patent: Oct. 16, 1990

[54] A METHOD AND DEVICE FOR IMPROVING THE DISCHARGE REGIME BETWEEN TWO ELECTRODES

[75] Inventors: Dominique Cathignol, Genas; Bernard Lacruche, Lyons; Jean-Louis Mestas, Chassieu, all of France

[73] Assignees: Technomed International, Paris; Institut National de la Sante et de la Recherche Medicale (INSERM), Lyons, both of France

[21] Appl. No.: 207,068

[22] Filed: Jun. 15, 1988

[30] Foreign Application Priority Data

Jun. 16, 1987 [FR] France ................................ 87 08400

[51] Int. Cl.5 ................................................ A61B 17/22

[52] U.S. Cl. .................................. 128/24 A; 367/147; 313/130; 313/131 A

[58] Field of Search ............. 128/24 A, 328; 367/142, 367/147; 313/130, 131 A, 232, 268, 269

[56] References Cited

U.S. PATENT DOCUMENTS 143,085 5/1920 Barker et al. .................... 313/131 A
1,960,142 5/1934 De Paniagua .
2,559,227 5/1947 Rieber ................................ 128/24 A
2,733,369 1/1956 Smits ................................ 313/131 A
3,222,567 12/1962 Smith ................................ 313/269
3,283,294 3/1965 Schrom ................................ 367/147
3,354,344 3/1967 Schrom ................................ 313/130
3,504,232 4/1967 Barbini ................................ 315/232
4,539,989 9/1985 Forssmann et al. ................ 128/328
4,868,791 9/1989 Cathignol et al. .................... 367/13

*Primary Examiner*—Kyle L. Howell
*Assistant Examiner*—K. M. Pfaffle
*Attorney, Agent, or Firm*—Schechter, Brucker & Pavane

[57] ABSTRACT

The invention relates to a method and to a device for improving the discharge regime of an electric arc produced between two electrodes. The device is characterized in that it includes means an insulating element (32), preferably spherical in shape, for increasing the resistance to the passage of the electric arc (A) between ends of the electrodes (12, 14). By using the invention it is possible to obtain an arc discharge of the critically damped type. The method and the device are preferably used in shock wave generator apparatus for hydraulic lithotripsy.

19 Claims, 2 Drawing Sheets

Invention

Invention

METHOD AND DEVICE FOR IMPROVING THE DISCHARGE REGIME BETWEEN TWO ELECTRODES

The invention relates essentially to a method and a device for improving the discharge regime of an electric arc produced between two electrodes, by interposing a high-resistance insulating element at least between the electrodes, and to a shock wave generator apparatus using such a method or such a device, in particular for hydraulic lithotripsy.

BACKGROUND OF THE INVENTION

Rieber U.S. Pat. No. 2,559,227 describes an apparatus for generating high frequency shock waves and comprising a reflector in the form of a truncated ellipsoid having shock waves generated by an electric arc or discharge between two electrodes converging on a first focus of the ellipsoid, thereby serving to destroy a target disposed at the second focus of the ellipsoid lying outside the truncated reflector.

The Reiber electrodes are made of highly conductive material such as copper or brass and are mounted on an insulator which is pivotally supported by a device serving to adjust the gap between the electrodes.

U.S. Pat. No. 3,942,531 describes a similar apparatus in which the liquid is constituted by water.

When using the Rieber apparatus or a similar apparatus, an electric arc or discharge is produced between the electrodes by suddenly discharging a capacitor by closing a high tension switch. In the Rieber apparatus, the circuit between the electrodes includes a capacitor and an associated self-inductor. It has been observed that the capacitor discharge is of the damped oscillating type. In other words, the capacitor discharges and then recharges in the opposite direction to a lower voltage than its initial voltage (which is very high and about 15,000 V to 20,000 V), and then recharges the initial way around, and so on until the charge contained in the capacitor has been lost.

Simultaneously, an electric arc is established between the two electrodes and as a result the associated current is also of the damped oscillating type.

When an electric arc or current is established between the two electrodes, the liquid, and in particular water, is vaporized, thereby generating a pressure wave or shock wave which can be used for destroying a target.

It will be understood, that the quicker the liquid, and in particular water, vaporizes, the stronger the pressure wave and the shorter its rise time.

Thus, in order to vaporize a large quantity of liquid, and in particular water, it is necessary to suddenly deliver a larger amount of energy.

All presently known devices give rise to discharges which are always of the damped oscillating type, which type is shown in FIG. *2a*of the present application, and the total energy dissipated over time is shown in accompanying FIG. *2b*. These figures are described in greater detail below, and the energy is dissipated progressively over time.

The main object of the present invention is therefore to solve the novel technical problem of delivering suddenly or in a relatively short length of time the major portion of the energy stored by charging the capacitor in the discharge circuit between two electrodes.

Another object of the present invention is to solve the novel technical problem of producing an initial pressure wave which is substantially spherical.

Yet another object of the, present invention is to solve the novel technical problem of reducing electrode wear.

These novel technical problems are solved in satisfactory manner for the first time by the present invention.

SUMMARY OF THE INVENTION

Thus, according to a first aspect, the present invention provides a method of improving the discharge regime of an electric arc produced in a fluid medium, in particular a low resistance medium such as water, said arc being produced between at least two arc-generating electrodes, wherein the resistance to the passage of the electric arc is increased at least between the electrodes.

In a particularly preferred implementation of the method in accordance with the invention, said resistance is increased by interposing a high resistance insulating element between the arc-generating electrodes This insulating element thus advantageously constitutes an obstacle to the direct passage of the arc between the electrodes.

According to another advantageous characteristic of the method of the invention, the resistance of the insulating element is selected in such a manner that said resistance causes arc discharge to be of the critically damped type.

According to another characteristic of the method of the invention, the shape of the insulating element is selected to be such that the initial pressure wave or shock wave created by generating the arc is substantially spherical. Preferably, the insulating element is essentially spherical in shape.

In a second aspect, the present invention also provides a device for improving the discharge regime of an electric arc produced in a fluid medium, in particular a low resistance medium such as water, between at least two arc-generating electrodes, the device comprising means for increasing the resistance to the passage of the electric arc at least between the electrodes.

In accordance with a particularly preferred embodiment, said means for increasing the resistance to the passage of the electric arc comprise a high resistance insulating element interposed between the arc-generating electrodes. The resistance and the shape of the insulating element may be defined as specified above with reference to the method.

Further, according to another advantageous characteristic, the insulating element includes two electrode-positioning cavities or grooves for the purpose of making it easy to position the arc-generating electrodes at a predetermined distance apart which is known in advance.

A presently preferred utilization of the method and of the device in accordance with the invention relates to a shock wave generator apparatus, and in particular to an apparatus including a reflector in the form of a truncated ellipsoid of the type described in Rieber's U.S. Pat. No. 2,559 227.

In this case, it is clear that the presence of the two above-mentioned cavities or grooves in the insulating element makes it possible to position the arc-generating electrodes in such a manner as to ensure that they are converging and symmetrically disposed relative to the internal focus of the truncated ellipsoidal reflector.

According to another advantageous characteristic of the present invention, the insulating element is fixed to a support rod mounted inside the ellipsoid. The support rod can be permanently fixed to the wall of the ellipsoid or it may removably mounted, while the insulating element is advantageously designed to be removable relative to the support rod.

It will thus be understood that all of the above-specified technical advantages are obtained

BRIEF DESCRIPTION OF THE DRAWINGS

An embodiment of the invention is described by way of example with reference to the accompanying drawings, in which.

DESCRIPTION OF PRESENTLY PREFERRED EMBODIMENT

Figure 1:
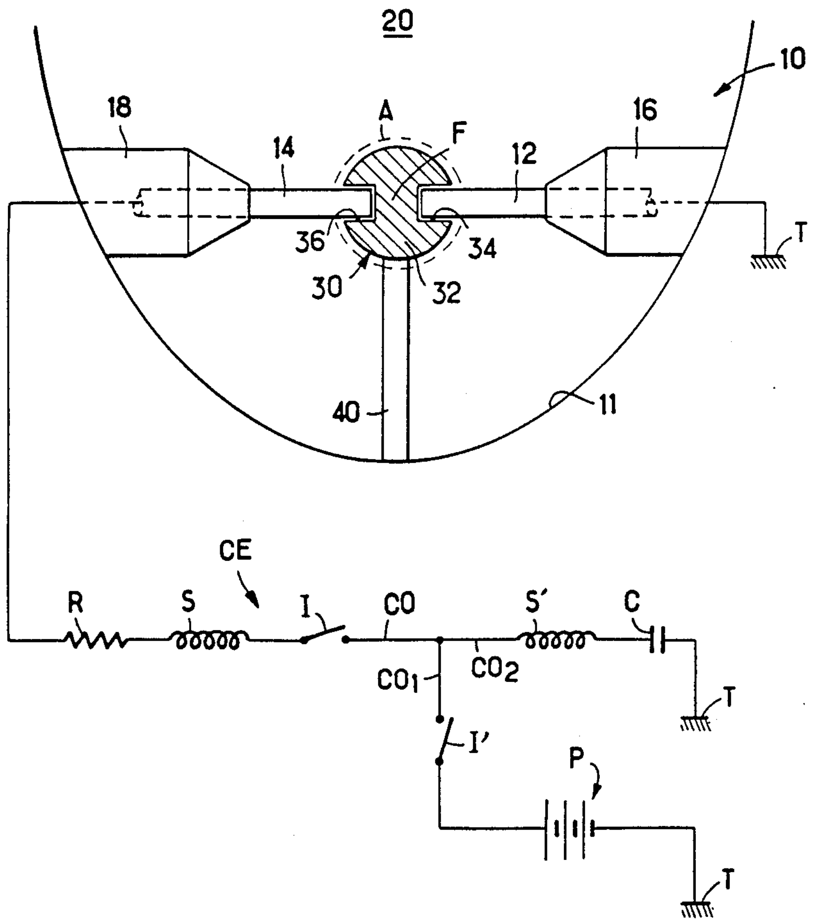
FIG. 1 is a fragmentary diagrammatic section view through a truncated ellipsoidal reflector, with the section plane passing through the electrodes and the internal focus of the truncated ellipsoidal reflector, and showing the circuit for charging the capacitor and for discharging it through the electrodes, said circuit being shown schematically.

FIG. 1 is a diagram showing a truncated ellipsoidal reflector of the type described in Rieber's U.S. Pat. No. 2,559,227 and given general reference numeral 10. It is provided with at least two diametrically opposite electrodes 12 and 14 which converge on the focus of the truncated ellipsoidal reflector 10 at the point marked F. The second focus of the ellipsoid lies outside the truncated ellipsoidal reflector and a target to be destroyed is caused to coincide with said second focus as described at length in Rieber's U.S. patent or in U.S. Pat. No. 3,942,531.

In general the electrodes 12 and 14 are mounted on electrode-carrier elements 16 and 18 which are also electrically conductive. One of the electrodes, for example the electrode 12, is connected to earth or ground as symbolized by the letter T.

The other electrode, for example the electrode 14, constitutes a part of an electric circuit given an overall reference CE and used to generate a very high voltage between the electrodes 12 and 14 when it is desired to set up an electric arc or discharge between the electrodes 12 and 14. In addition, the cavity defined inside the truncated ellipsoidal reflector 10 is filled with a fluid and preferably a liquid, which liquid is preferably water. The electric arc will give rise to pressure waves or shock waves at the internal focus F of the truncated ellipsoidal reflector 10 and these waves will be focused on the second focus where the target to be destroyed is located, in conventional manner.

For example, running from the electrode 14, the electric circuit CE may comprise: a conventional resistor R followed by an inductor S and then a switch I. Thereafter, the conductor CO splits into two conductors $CO_1$ and $CO_2$. Conductor $CO_2$ then passes through another inductor S' and a capacitor C which is designed to withstand charging to very high voltages of up to 15,000 V to 20,000 V, for example, said capacitor C then being connected to ground T. The other conductor $CO_1$ leads to another switch I' which is then connected to a source for generating power P, for example a battery, optionally with a transformer interposed between the switch I' and the power generator P for the purpose of transforming the low voltage from the power generator P to a very high voltage, e.g. a voltage of about 15,000 V to 20,000 V. Thereafter, the power generator P is also connected to ground.

It will thus be understood that when the switch I is open, as shown, and the switch I' is closed, the capacitor C is charged from the power generator P. Thereafter, when the switch I' is opened, as shown, and the switch I closed, then the capacitor C discharges via the electrodes 12 and 14, since the circuit $CO$—$CO_2$—$T$ is closed.

Figure 2A:
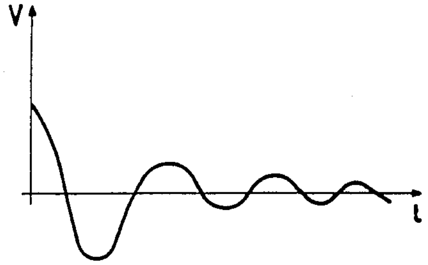
Fig.2a Prior art
FIG. 2*a* is a graph showing capacitor voltage as a function of time during capacitor discharge in accordance with the prior art and showing that it is of the damped oscillating type.

In the conventional case as described in Rieber's abovementioned U.S. patent or in U.S. Pat. No. 3,942,531, an electric arc of the damped oscillating type is obtained because of the discharge curve of the capacitor which is itself of the damped oscillating type as shown in FIG. 2*a*. This is due to the fact that the capacitor C will discharge and then recharge partially in the opposite direction to a voltage which is lower than the initial voltage of about 15,000 V to 20,000 V, and will then recharge partially in the initial direction, and so on, until all of the charge contained in the capacitor has been lost. As a result, the current constituting the electric arc between the electrodes is also of the damped oscillating type, and will have a curve as a function of time which is similar to that shown in FIG. 2*a*.

Figure 2B:
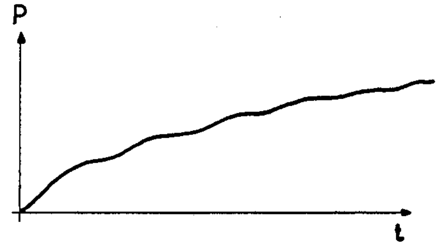
Fig.2b Prior art
FIG. 2*b* shows the energy $P=RI^2$, dissipated, as a function of time and due to the voltage curve shown in FIG. 2*a*, wherein it can be seen that the energy is dissipated progressively over time.

The curve of energy dissipation P obtained from such a conventional discharge of the capacitor C is shown in FIG. 2*b*, and it can be seen that the energy stored in the capacitor is dissipated progressively over time. As a result, the pressure waves or shock waves which are generated by the sudden passage of electric current or arcing between the electrodes fall off progressively in amplitude (i.e. they contain less energy P), and as a result a succession of waves is thus generated having less and less energy.

Unfortunately, in order to destroy the target located at the second focus of the truncated ellipsoidal reflector 10, it is necessary to generate substantially instantaneously a shock wave having pressure which is as high as possible, i.e. having the highest possible energy. It is therefore necessary to deliver as much energy as possible suddenly and in the shortest possible period of time.

As mentioned above, the object of the present invention is to solve this novel technical problem posed by the inventors.

This is done, according to the invention, by providing means given an overall reference numeral 30 for increasing the resistance to the passage of the electric arc at least between the electrodes 12 and 14.

In the presently preferred embodiment, said means 30 for increasing resistance to the passage of an electric arc comprises a high resistance insulating element 32 interposed between the arc-generating electrodes 12 and 14.

The term "high resistance" is used herein to indicate that the resistance of the insulating element is much greater than the resistance of the fluid medium filling the cavity 20 of the truncated ellipsoidal reflector 10. The resistance ratio between said insulating element and the fluid medium filling the ellipsoidal reflector 10 should at least 100. and is preferably equal to at least 1,000 or several tens of thousands. It is advantageous for the resistance of the insulating member to at least several tens of thousands times the critical resistance of the discharge circuit (which is usually several ohms).

Figure 3A:
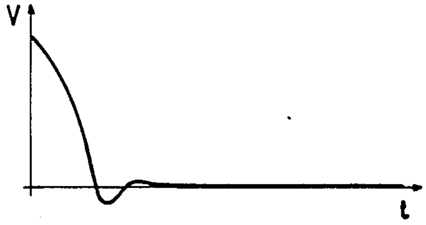
FIG. 3*a* is a graph of the capacitor voltage as a function of time during capacitor discharge as obtained when applying the present invention, and it can be seen that the discharge curve obtained in accordance with the invention is of the critically damped type.

According to another particularly advantageous characteristic of the invention, the insulating element has a resistance such that its resistance gives rise to an arc discharge of the critically damped type, thereby also discharging the capacitor C in critically damped manner, with said discharge curve being shown in FIG. 3*a*.

It has been observed that this critically damped discharge regime of the capacitor C can be obtained using numerous insulating materials. In accordance with the invention, it is highly practical to make use simply of ceramics, with ceramics normally having a resistance equal to about 100 kΩ.

In accordance with a particularly advantageous characteristic of the device of the invention, the insulating element is substantially spherical in overall shape, thereby serving to generate an initial pressure shock wave which is substantially spherical. When the device in accordance with the invention is used in a shock wave generator apparatus, as shown in FIG. 1, and in particular apparatus an of the type having a truncated ellipsoidal reflector 10, it will be understood that it is advantageous for the center of the sphere constituting the insulating element 32 to coincide substantially exactly with the internal focus F of the truncated ellipsoidal reflector 10.

Further, it is advantageous in accordance with the invention for the insulating element 32 (which is preferably substantially spherical in shape) to include two cavities or grooves 34 and 36 for receiving the electrodes 12 and 14, as shown in FIG. 1, in such a manner that when the ends of the electrodes 12 and 14 come into abutment against the bottoms of the cavities 34 and 36 in the insulating element 32, the electrodes converge symmetrically on the focus F of the truncated ellipsoidal reflector 10. It will be understood that this specific structure ensures that the electrodes 12 and 14, when in abutment against the bottoms of the cavities 34 and 36, are permanently disposed exactly symmetrically about the focus F of the ellipsoid defined by the truncated ellipsoidal reflector 10. As a result, the shock waves will have a wave front which is exactly centered on the focus F.

It will be understood that the essentially spherical shape of the insulating element 32 and its insulating nature serve to cause the insulating element 32 to constitute an obstacle to the passage of lines of current which are obliged to move round the obstacle.

Thus, the size of the element 32 is selected experimentally in such a manner as to ensure that a critically damped discharge is obtained (see FIG. 3*a*).

Further, by using an insulating element 32 which is substantially spherical in shape, the lines of current generated between the electrodes 12 and 14 and represented by dashed lines referenced A are also essentially spherical in shape and therefore generate shock waves which are exactly centered on the focus F.

Figure 3B:
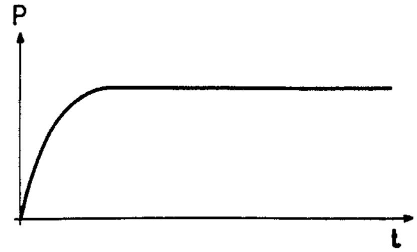
FIG. 3*b* shows the corresponding curve of energy dissipation as a function of time resulting from the FIG. 3*a* voltage curve in accordance with the invention

By virtue of the critically damped discharge regime for the capacitor C thus obtained in accordance with the invention, energy dissipation will correspond to the curve shown in FIG. 3*b*, thus giving rise to a substantially unique wave of very high pressure, thus providing better efficiency in destroying targets.

Further, by virtue of this discharge which is obtained substantially once only, an unexpected reduction is obtained in the wear of the various elements, and in particular in the wear of the electrodes, of the capacitor C, and of the high tension switch I which withstands reverse voltages and currents poorly.

Further, since electrode wear is unavoidable and due to generating successive electric arcs between the electrodes, and since such wear is, in addition, unequal between the electrodes, the electrodes need repositioning so as to be exactly symmetrically disposed relative to the focus F.

In general, electrode-advance devices are provided. Such devices are described, for example, in U.S. Pat. No. 4,608,983, but preferably, electrode-advance devices as described in commonly owned U.S. Pat. No. 4,730,614 are used. Also preferably, electrode-advance devices of the type described in said prior patent are used after being modified in such a manner that drive is performed by pneumatic means engaging a friction system so as to maintain the front ends of the electrodes 12 and 14 permanently in contact with the bottoms of the cavities 34 and 36 in the insulating element 32. This makes it possible to keep the front ends of the electrodes 12 and 14 permanently maintained exactly symmetrically about the focus F, and thus at exactly equal distances from the focus F.

This gives rise to an additional improvement in apparatus operation, and thus to an improvement in target destruction.

In practice, the insulating element 32 is supported on support means in the form of a rod 40 which may be mounted on the inside of the wall 11 of the truncated ellipsoidal reflector 10. The support means 40 may be permanently mounted or they may be mounted in removable manner or they may possibly be retractable or telescopic. The material from which the rod 40 is made is advantageously an insulating material, and its diameter should be as small as possible so as to interfere as little as possible with the shock waves generated on the same side as the support means.

It will be understood that the device described above makes it possible to implement the above-defined method which is not described in further detail. The same applies to operation of the device which results clearly from the above description which already contains an explicit explanation of operation for a person skilled in the art.

Naturally the scope of the invention extends to means constituting technical equivalence of the means described and shown in FIGS., 1, 3*a*, and 3*b*., and such equivalent means form a part of the invention.

We claim:

1. A method of improving a discharge regime of an electric arc produced in a low electrical resistance fluid medium, said arc being produced in said medium between at least two axially aligned arc-generating electrodes having their free ends disposed in axially spaced apart relation for defining a gap between same, the method comprising increasing the electrical resistance in said gap above the resistance of said fluid medium for modifying the shape of the electrical arc generated therebetween.

2. A method according to claim 1, wherein said step for increasing the electrical resistance in said gap comprises disposing a high resistance insulating element in the gap between the free ends of the electrodes.

3. A method according to claim 2, wherein the resistance of the insulating element is selected in such a manner as to cause said resistance to give rise to an arc discharge of a critically damped type.

4. A method according to claim 2, wherein the step of disposing a high resistance insulating element in said gap further comprises selecting the shape of the insulating element in such a manner as to ensure that the arc is substantially spherical in shape.

5. The method of claim 1, wherein the medium is a liquid.

6. A device for improving a discharge regime of an electric arc produced in a low electrical resistance medium between at least two axially aligned arc-generating electrodes having their free ends disposed in axially spaced apart relation for defining a gap therebetween, the device comprising means for increasing the electrical resistance in said gap above the electrical resistance of said medium, thereby modifying the shape of the electrical arc generated between the free ends of the electrodes.

7. A device according to claim 6, wherein the means for increasing the electrical resistance in said gap comprises a high resistance insulating element interposed in the gap.

8. A device according to claim 7, wherein the resistance of the insulating element is selected to induce an arc discharge of an essentially critically damped type.

9. The device of claim 6, wherein the medium is a liquid.

10. A device for improving a discharge regime of an electric arc produced in a low electrical resistance medium, said electric arc being produced between at least two axially aligned, arc-generating electrodes having their free ends disposed in axially spaced apart relation for defining a gap therebetween, said device comprising a high resistance insulating element interposed in said gap between the free ends of the electrodes, the insulating element being substantially spherical in shape.

11. A device according to claim 10, wherein the insulating element includes two electrode-positioning cavities defined by bottom walls, such that when the free ends of the electrodes are in abutment against the bottom walls of the cavities, the free ends of the electrodes converge symmetrically about a focus point on which the electric arc is to be centered.

12. A shock wave generator apparatus comprising a truncated ellipsoidal reflector having a first focus internal to said reflector and a second focus lying outside said reflector, said reflector being filled with a low electrical resistance liquid; at least two axially aligned, arc-generating electrodes having their free ends disposed in axially spaced apart relation for defining a gap therebetween, said free ends of said electrodes being immersed in said liquid; a high electrical resistance insulating element interposed in the gap between the free ends of the electrodes; and a support means mounted inside said truncated ellipsoidal reflector for supporting said insulating element.

13. The shock wave generator of claim 12, wherein the insulating element has a geometric center located in coincidence with the internal focus of the ellipsoidal reflector.

14. The shock wave generator apparatus of claim 12, wherein the insulating element is substantially spherical in shape.

15. The shock wave generator of claim 12, wherein the liquid is water.

16. A shock wave generator apparatus for generating a shock wave by generating an electric arc between arc-generating electrodes, said apparatus comprising a chamber filled with a low electrical resistance liquid, two arc-generating electrodes axially aligned and having their free ends disposed in axially spaced apart relation for defining a gap therebetween, at least said free ends of the electrodes being disposed in said liquid in said chamber, said apparatus further comprising means for increasing the electrical resistance in said gap between the free ends of the electrodes for modifying the shape of the electrical arc generated therebetween.

17. A shock wave generator apparatus for generating a shock wave by generating an electric arc between two arc-generating electrodes, said apparatus comprising a chamber filled with a low electrical resistance liquid two arc-generating electrodes axially aligned and having their free ends disposed in axially spaced apart relation for defining a gap therebetween, said free ends of the electrodes being disposed in said liquid in said chamber, said apparatus further comprising a high resistance insulating element interposed in said gap between the free ends of the electrodes, said insulating element constituting an obstacle to the direct passage of the electric arc between the free ends of the electrodes.

18. A shock wave generator apparatus according to claim 17, wherein said chamber includes a truncated ellipsoidal reflector, a support means comprising a rod mounted inside said truncated ellipsoidal reflector for supporting said insulating element, and said high resistance insulating element having a center with the center of the insulating element coinciding with the internal focus of the ellipsoidal reflector.

19. In a process for generating a shock wave in a shock wave generator by generating an electric arc between two electrodes, said electrodes being axially aligned and having their free ends disposed in axially spaced apart relation for defining a gap therebetween, the free ends of the electrodes being immersed in a low electrical resistance liquid medium, wherein the improvement comprises a step of increasing the electrical resistance in said gap between the free ends of the electrodes thereby modifying the shape of the electrical arc generated therebetween.

* * * * *

UNITED STATES PATENT AND TRADEMARK OFFICE

CERTIFICATE OF CORRECTION

PATENT NO. : 4,962,753

DATED : October 16, 1990

INVENTOR(S) : Dominique Cathignol, et al.

It is certified that error appears in the above-identified patent and that said Letters Patent is hereby corrected as shown below:

On the title page, in item [57] ABSTRACT, line 4, after "includes", delete "means".

Column 2, line 4, delete the comma after "the".

Column 8, line 31 (claim 17, line 4), after "liquid", insert --,--.

Signed and Sealed this

Ninth Day of June, 1992

Attest:

DOUGLAS B. COMER

Attesting Officer

Acting Commissioner of Patents and Trademarks